(12) United States Patent
Berner et al.

(10) Patent No.: US 10,342,642 B2
(45) Date of Patent: Jul. 9, 2019

(54) DENTAL IMPLANT OR ABUTMENT COMPRISING A CERAMIC BODY COVERED WITH A MONOMOLECULAR PHOSPHATE LAYER

(71) Applicant: STRAUMANN HOLDING AG, Basel (CH)

(72) Inventors: Simon Berner, Basel (CH); Heiner Bieli, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 876 days.

(21) Appl. No.: 14/431,554

(22) PCT Filed: Sep. 23, 2013

(86) PCT No.: PCT/EP2013/002853
§ 371 (c)(1),
(2) Date: Mar. 26, 2015

(87) PCT Pub. No.: WO2014/048555
PCT Pub. Date: Apr. 3, 2014

(65) Prior Publication Data
US 2015/0272708 A1  Oct. 1, 2015

(30) Foreign Application Priority Data
Sep. 26, 2012 (EP) .................................. 12006714

(51) Int. Cl.
*A61C 8/00* (2006.01)
(52) U.S. Cl.
CPC ............ *A61C 8/0015* (2013.01); *A61C 8/005* (2013.01); *A61C 8/0013* (2013.01);
(Continued)

(58) Field of Classification Search
CPC ...... A61C 8/0015; A61C 8/0013; A61C 8/005; A61C 8/0012; A61C 2008/0046; C04B 28/34
(Continued)

(56) References Cited

U.S. PATENT DOCUMENTS 5,123,844 A     6/1992  Wakai et al.
6,428,579 B1 *  8/2002  Valentini ............. A61F 2/30767
                                                     427/2.13
(Continued)

FOREIGN PATENT DOCUMENTS

EP     0404123 A2    12/1990
EP     2002799 A1    12/2008
(Continued)

OTHER PUBLICATIONS

May 12, 2013 International Search Report issued in International Patent Application No. PCT/EP2013/002853.
(Continued)

*Primary Examiner* — Wade Miles
*Assistant Examiner* — Gwen M Demosky
(74) *Attorney, Agent, or Firm* — Oliff PLC (57) ABSTRACT

The present invention refers to a dental implant or abutment including a ceramic body having a surface, the ceramic body including zirconia as the main component. At least a first surface area of the ceramic body is covered with an at least essentially monomolecular phosphate layer having a thickness of less than 1.0 nm. The phosphate layer contains phosphates selected from the group consisting of orthophosphate, poly-phosphates, cyclo-phosphates, and mixtures thereof. Furthermore, a kit including a gas- and liquid-tight container, with the dental implant or abutment being stored inside the container, and a method for the preparation of the dental implant or abutment are disclosed.

20 Claims, 1 Drawing Sheet

(52) U.S. Cl.
CPC .......... *A61C 8/0037* (2013.01); *A61C 8/0087* (2013.01); *A61C 2008/0046* (2013.01)

(58) Field of Classification Search
USPC ............ 433/172–176, 201.1; 427/2.26, 2.29; 606/76, 77, 300, 301, 331
See application file for complete search history.

(56) References Cited

U.S. PATENT DOCUMENTS

| | | | |
|---|---|---|---|
| RE43,793 E | 11/2012 | Descouts et al. | |
| 2004/0049287 A1* | 3/2004 | Descouts | A61C 8/0012 |
| | | | 623/23.6 |
| 2004/0054422 A1 | 3/2004 | Descouts et al. | |
| 2010/0036502 A1* | 2/2010 | Svrluga | A61C 8/0012 |
| | | | 623/23.6 |
| 2010/0131062 A1* | 5/2010 | Andersson | A61L 27/04 |
| | | | 623/11.11 |
| 2010/0234900 A1 | 9/2010 | Descouts et al. | |
| 2010/0280601 A1* | 11/2010 | Hofer | A61B 5/14546 |
| | | | 623/1.46 |
| 2012/0041541 A1* | 2/2012 | Bayer | A61L 31/022 |
| | | | 623/1.15 |
| 2012/0258148 A1 | 10/2012 | Descouts et al. | |
| 2012/0288699 A1* | 11/2012 | Ahlberg | A61L 27/04 |
| | | | 428/220 |

FOREIGN PATENT DOCUMENTS

| | | | |
|---|---|---|---|
| JP | 2008-099953 A | 5/2008 | |
| WO | 02/40073 A1 | 5/2002 | |

OTHER PUBLICATIONS

May 12, 2013 International Written Opinion issued in International Patent Application No. PCT/EP2013/002853.

* cited by examiner

DENTAL IMPLANT OR ABUTMENT COMPRISING A CERAMIC BODY COVERED WITH A MONOMOLECULAR PHOSPHATE LAYER

The present invention relates to a dental implant or abutment comprising a ceramic body, to a kit comprising a container and the dental implant or abutment, and to a method for preparing said dental implant or abutment.

Implants, such as dental implants, are well known in the art. They generally consist of a material, which is biocompatible and which additionally has a low elastic modulus and a high strength.

Apart from its biocompatibility and its mechanical properties, the osteointegrative properties of an implant are usually of major importance. The term "osteointegration" designates the direct structural and functional connection between living bone and the surface of the load-bearing implant. A good osteointegration means that the implant, after reaching a primary stability by screwing it into the bone, safely ossifies within a short healing time so that a permanent bond between implant and bone is obtained.

Dental implants and abutments, which are currently in use, are in general made of a metal, e.g. titanium, or of a ceramic, e.g. a zirconia based ceramic, due to the biocompatibility and the favourable mechanical properties of these materials.

In contrast to metal implants, which are generally dark, ceramic materials have the advantage that their colour can be closely matched to the natural tooth colour. Efforts have thus been made to provide dental implants, and in particular abutments, of which at least those parts that are visible after placement into a patient's jaw are made of a ceramic material.

In order to achieve optimal osteointegration of the implant, several surface treatments have been developed:

EP 1 450 722 relates to a dental implant made of zirconia ceramic, which, after abrasive blasting, is subjected to a treatment using phosphoric acid, sulphuric acid, hydrochloric acid or mixtures thereof.

EP 1 982 670 discloses a process for providing the implant with a surface roughness by sandblasting, milling and/or injection molding techniques, followed by etching with a hydrofluoric acid solution.

As an alternative to the above subtractive processes, it is also well known to provide the implant surface with a suitable coating in order to improve its osteointegrative properties. Such coatings include, for instance, metallic or ceramic coatings, hydroxylapatite coatings or coatings comprising bioactive factors, such as bone growth enhancing factors or bone morphogenic proteins.

US 2003/0157349 refers to an osteoconductive biomaterial including a metallic or oxide ceramic substrate and a metal oxide layer on the surface of the substrate, which contains at least on a portion of the oxide layer a coating comprising dihydrogenphosphate, titanium hydroxide, zirconium hydroxide, niobium hydroxide, tantalum hydroxide or silicon hydroxide. Said coating is formed by soaking the substrate in a phosphate buffer or a similar solution and subjecting it to hydrothermal treatment at a temperature of 100° C. or higher and a pressure of 0.1 MPa or higher. In the surfaces thus obtained, the chemical species, which has been applied, is typically found in a depth range of about 0.1 to 0.8 μm.

When providing a ceramic body with such a coating, it is important that the advantageous properties of the ceramic material are not lost due to the coating. Also, the applied coating material must not have any undesired side effect once implanted in the human body. For this reason, thin, phosphorus-based coatings have been chosen in the past:

US 2006/0194008 discloses devices made of titanium having multiple surface functionality, which have been provided with phosphorus-based coatings. The coatings have a plurality of phosphate moieties, a plurality of phosphonate moieties or both, which are covalently bonded to an oxide surface of an implantable substrate. According to a preferred embodiment, these phosphorus-based coatings have a thickness of less than about 10 nm.

According to one embodiment of US 2006/0194008, the device surface is treated with phosphoric acid at a pH of less than 3. Due to these rather harsh conditions, the titanium surface of the devices is partially dissolved and three dimensional titanium phosphate complexes are formed. Since a ceramic surface is inert under these conditions, it is not possible to apply an analogous coating to a ceramic surface. Furthermore, the surface structure of the devices is significantly changed by the application of the titanium phosphate complexes.

U.S. Pat. No. 4,962,073 refers to surface treated porous ceramic membranes comprising a metal oxide/hydroxide. Chemically bonded to the metal oxide/hydroxide surface of the membrane is a monomolecular layer of one or more phosphoric acid esters.

Also WO 02/40073 discloses endosseous implants, the surface of which has been treated with at least one organic compound carrying at least one phosphonic acid group or a salt thereof. It is assumed that these phosphonates form a covalent bond with the surface of the implant.

US 2010/0131062 relates to a method of applying crystalline nanoparticles onto the surface of an implant to produce an implant with a crystalline nanoparticle layer on its surface. For implants, calcium phosphate and hydroxylapatite nanoparticles have been found to be suitable. However, said nanoparticles are forming a crystalline layer on the surface, which may peel off under mechanical stress.

For a good integration of a dental implant, it is not only important that a strong bond to the bone is formed (i.e. good osteointegration), but also that the implant has no adverse effect on the soft tissue. In this respect, it has been found that also the soft tissue integration of an implant or abutment plays a crucial role for the overall healing after placement of a dental implant.

As a consequence, dental implants and abutments have also been subjected to various surface treatments in order to improve the soft tissue integration. For instance, it has been found that a roughened, hydroxylated and hydrophilic surface has a positive effect on the soft tissue integration (see e.g. EP 1 825 828, EP 1 825 829 or EP 1 825 830).

The problem of the present invention is to provide a dental implant or abutment made of ceramic, which is characterized by a particularly good integration.

The problem is solved by the dental implant or abutment according to claim 1, the kit comprising a container and the dental implant or abutment according to claim 12, and the method for preparing said dental implant or abutment according to claim 14. Preferred embodiments are subject of the dependent claims.

The present invention features a dental implant or abutment comprising a ceramic body having a surface. The ceramic body comprises zirconia (i.e. zirconium oxide) as the main component. The dental implant or abutment is characterized in that at least a first surface area of the ceramic body is covered with an at least essentially monomolecular phosphate layer having a thickness of less than 1.0 nm. Therefore, at least part of the surface area of the ceramic body is covered with a relatively thin phosphate layer. The phosphate layer contains at least one phosphate selected from the group consisting of ortho-phosphate, poly-phosphates, cyclo-phosphates, and mixtures thereof. Thus, the present invention refers to a dental implant or abutment with a zirconia-based ceramic body, the surface of which is at least partially covered with an at least essentially monomolecular phosphate layer having a thickness of less than 1.0 nm.

A "dental implant", as used throughout this application, is an implant used in the dental field for replacement of one or more teeth or at least part of a tooth. In general, a dental implant comprises at least an anchoring part for anchoring the implant in the jaw bone and a mounting part for attachment of an abutment, a crown or a similar element. The dental implant of the present invention is not limited to any particular shape, and may in particular be a one- or two-part implant as generally known in the field.

An "abutment", as used throughout this application, is a separate mounting part for a dental implant, which is intended for attachment to the dental implant and to a crown. Again, the abutment of the present invention is not limited to any particular shape.

The ceramic body of the dental implant or abutment of the present invention comprises zirconia as the main component. Thus, the ceramic body is made of a zirconia-based material. Zirconia shows no interactions with other dental materials and is electrically neutral. Because of a friendly gum reaction and due to the fact that dental plaque seems to be less attached to this material, it bears also a low risk of inflammation. In addition, zirconia has a light colour and can thus be closely adapted to natural tooth colour. Also, the ceramic body of the present invention is highly resistant, biocompatible and can be worked into the desired shape for a dental implant or abutment.

An "at least essentially monomolecular layer", as used throughout this application, is a thin layer of a material covering the surface of the ceramic body, the thickness of the layer being not more than about one molecule. For instance, such a phosphate layer may have a thickness of about 0.7 to about 1.3 phosphate molecules. Thus, in the planar direction, the phosphate layer may have any dimension, while it is limited to about one molecule in the orthogonal direction. Further, the phosphate layer may be uniform or irregular, and may also have small gaps in the lateral direction. Therefore, it is not necessary that the phosphate molecules occupy every single adsorption site on the ceramic surface. In order for the implant or abutment surface to be hydrophilic, it is believed that only about 10% of the adsorption sites on the surface of the ceramic body need to be occupied, which is comparable to a 3×3 superlattice. However, a more dense arrangement of the phosphate molecules on the ceramic surface is preferred.

Preferably, the dental implant or abutment of the present invention comprises a ceramic body that is covered with a monomolecular phosphate layer. In this case, the phosphate layer has a thickness of one phosphate molecule within the measuring accuracy.

A "phosphate", as used throughout this application, is a phosphate group that does not comprise any organic substituents. In particular, the phosphates of the present invention do not include phosphate esters or phosphonates.

Surprisingly, it has been found that a ceramic dental implant or abutment with such a thin phosphate layer has exceptionally good osteointegrative properties. This can at least partially be explained by the finding that the hydrophilicity of the ceramic body's surface is increased by the phosphate covering, since a good hydrophilicity generally goes along with a good osteointegration.

Furthermore, it is believed that the phosphates on the surface lead to a beneficial interaction with the surrounding bone tissue, thereby further improving the formation of a bond between bone and implant surface. Also, in contrast to the phosphoric acid esters of U.S. Pat. No. 4,962,073, for instance, the phosphates in the covering layer of the present invention are directly available for incorporation into newly formed bone, whereas the phosphoric acid esters require previous hydrolysis.

Also, the interaction between the surrounding soft tissue and the implant/abutment has been found to be beneficial, probably thanks to the phosphate layer on the ceramic surface.

It is believed that, thanks to the thinness of said layer, the surrounding bone or soft tissue is able to interact with both the phosphate groups and the ceramic material, leading to a particularly good connection between ceramic body and bonesoft tissue. Furthermore, the coating of the present invention is not prone to peeling off, which is a well-known problem of thicker coatings. Also, even if the coating is degraded in the patient's body, there is essentially no gap between implant or abutment and surrounding bonesoft tissue, such that the stability is always guaranteed.

As a further advantage, the thin phosphate layer of the present invention does not change the topography of the underlying ceramic surface. Therefore, in case the ceramic body has been provided with a special surface structure, such as a smooth or roughened surface, this structure will be conserved upon application of the phosphate layer.

Also, it has been found that the dental implant or abutment of the present invention is very well integrated in soft tissue, thereby further enhancing the good healing properties after implantation.

By X-ray photoelectron spectroscopy (XPS) analysis of the surface, it has been shown that the ceramic material is visible through the thin phosphate coating. For the claimed zirconia-based ceramic, it has been found that still about 20 (atomic) % zirconium is detected. Therefore, the outermost surface layer is still influenced by the ceramic material, which will have a positive effect on the attachment of the surrounding tissue.

In addition, there is a strong bond between the ceramic surface and the phosphate layer thereon, such that the phosphate layer does not delaminate during transport or storing. Therefore, the ceramic body of the present invention is also very stable.

In the early state of the art, rather thick phosphate coatings have been discussed. These phosphate coatings are typically several micrometers thick, which is several orders of magnitude more than the monomolecular phosphate layers of the present invention. The previously known thick phosphate coatings have several disadvantages: The connection between phosphate layer and ceramic surface is not very strong, therefore the phosphate coating may peel off during transport or storing. Also, the thickness of these phosphate coatings is inhomogeneous.

Furthermore, upon insertion of the ceramic body into bone, the high phosphate concentration may lead to irritation of the surrounding (soft) tissue and thereby even cause an inflammation. Therefore, the physiologic conditions in the surrounding area are severely disturbed, which may impair the osteointegration and ultimately lead to loss of the implant.

In addition, the thick phosphate coatings also significantly modify the surface morphology of the ceramic body, whereas the very thin layers of the present invention essentially preserve the surface morphology (see FIGS. 1a-c and 2a-c).

In contrast to the present invention, the phosphorus-based coatings of US 2006/0194008 are formed on a titanium surface and at a very low pH. By the described procedure, the surface is partially corroded and titanium phosphate complexes are formed.

U.S. Pat. No. 4,962,073 and WO 02/40073, on the other hand, disclose only coatings with phosphates bearing organic substituents, namely phosphate esters and phosphonates, respectively.

And the crystalline nanoparticle layers of US 2010/0131062 have a thickness of 2 nm to 500 nm.

Consequently, the coatings of US 2006/0194008, U.S. Pat. No. 4,962,073, WO 02/40073 and US 2010/0131062 are not comparable to those of the present invention and do not provide the desired improved integration properties.

In a preferred embodiment of the present invention, the monomolecular phosphate layer has a thickness of about 0.5 nm. It has been found that the osteointegration of the dental implant or abutment is particularly good in this case. Furthermore, the bonding of this at least essentially monomolecular layer to the implant or abutment surface is particularly strong. Also, the at least essentially monomolecular phosphate layer is able to form an optimal transition from the zirconia surface to the surrounding bone.

According to a preferred embodiment, the phosphate is selected from the group consisting of ortho-phosphate, di-phosphate, tri-phosphate, trimeta-phosphate, and mixtures thereof. Particularly preferred is the use of ortho-phosphate. As mentioned above, all these phosphates do not have any organic substituents, i.e. they are directly derived from the pertaining phosphoric acids by simple deprotonation. Ortho-phosphate ($PO_4^{3-}$), for instance, is the phosphate derived from ortho-phosphoric acid ($H_3PO_4$).

In general, the implant has a bone contact area and/or a soft tissue contact area. The bone contact area is that part of the implant surface, which is intended to be in contact with the bone (for a dental implant: the jaw bone) after implantation; the soft tissue contact area is that part of the implant surface, which is intended to be in contact with the soft tissue after implantation. In a modern dental implant, at least part of the bone contact area is typically provided with a thread, whereas the soft tissue contact area is usually threadless. Both the bone contact area and/or a soft tissue contact area may be roughened or smooth, with the bone contact area preferably being roughened and the soft tissue contact area preferably being smooth. Also, there may be a transition area between the bone contact area and the soft tissue contact area, which may have the same characteristics of either contact area or, in case the bone contact area and the soft tissue contact area are different, the transition area may form a transition from one state to the other or correspond in one characteristic to the bone contact area and in another to the soft tissue contact area.

Depending on the type of dental implant, it comprises both a bone contact area and a soft tissue contact area or only a bone contact area. In either case, it is preferred that at least the bone contact area of the ceramic body is covered with the thin phosphate layer. Thereby, an optimal osteointegration is achieved.

According to a preferred embodiment, both the bone and the soft tissue contact area of the dental implant are covered with the phosphate layer. It has surprisingly been found that due to the improved hydrophilicity achieved according to the present invention, not only a positive effect on the bone/implant interface can be obtained. Also, the contact of the implant's soft tissue contact area with the soft tissue has been found to be improved, although it is assumed that the mechanisms underlying this improvement are different from those underlying the osteointegration.

A dental implant system typically comprises an anchoring part for anchoring the dental implant in a jaw bone and a mounting part for attaching a suprastructure, such as a crown. According to a preferred embodiment, at least the surface of the anchoring part is covered with the phosphate layer. More preferably, the surface of both the anchoring part and the mounting part are covered with the phosphate layer.

It is particularly preferred that the entire surface of the ceramic body is covered with a phosphate layer. This allows for uniform treatment of the entire surface of the dental implant or abutment.

In a preferred embodiment, the ceramic body is made of stabilized zirconia. More preferably, the ceramic body is made of yttria-stabilized zirconia, ceria-stabilized zirconia, magnesium oxide stabilized zirconia or alumina-stabilized zirconia (ATZ). However, also other ceramic materials comprising zirconia, such as zirconia-stabilized alumina, or zirconia-based materials comprising more than one stabilizer are possible.

According to the most preferred embodiment, the ceramic body of the dental implant or abutment of the present invention is made of yttria-stabilized zirconia. In general, the yttria-stabilized zirconia is tetragonal in phase. Yttria-stabilized zirconia displays a very high strength, a high toughness and a good wear resistance.

In a particularly preferred embodiment, the ceramic body is made of yttria-stabilized zirconia according to ISO 13356. An example of a preferred yttria-stabilized zirconia is Tosoh zirconia powder of grade TZ-3YSB-E (Tosoh Corporation) comprising 4.95 to 5.35 wt-% $Y_2O_3$, 0.15 to 0.35 wt-% $Al_2O_3$, at most 0.02 wt-% $SiO_2$, at most 0.01 wt-% $Fe_2O_3$, at most 0.04 wt-% $Na_2O$ and comprising a binder in an amount corresponding to an Ig-loss of 2.7 to 3.9 wt-%, the percentages being based on the total weight of the zirconia powder.

In a preferred embodiment, the dental implant or abutment of the present invention is stored in water, which may optionally also contain one or more additives. Suitable additives include, for instance, $Na^+$, $K^+$, $Mg^{2+}$, $Sr^{3+}$, $Cl^-$, $PO_4^{3-}$, $HPO_4^{2-}$, and $H_2PO_4^-$. Preferably, these additives have been added to the water in the form of their respective salts. Additionally or alternatively, the water can also contain suitable gases, such as oxygen, inert gases and/or $CO_2$.

More preferably, the dental implant or abutment of the present invention is stored in an aqueous phosphate solution, preferably in an aqueous phosphate buffer solution. Said aqueous phosphate solution contains phosphates, typically in a concentration of 1 mM to 3 M, preferably of 20 mM to 1 M, and more preferably of 50 mM to 0.5 M, and usually has a pH of 4 to 10, preferably 5 to 9, more preferably 6 to 8.

In a further aspect, the present invention also relates to a kit comprising a gas- and liquid-tight container and the dental implant or abutment of the present invention. Within this kit, the dental implant or abutment is stored in the container, i.e. it is arranged inside the container.

Dental implants and abutments are generally packaged prior to storing and delivery to a surgeon in order to avoid contamination of the dental implant or abutment. Furthermore, by storing the dental implant or abutment in a gas- and liquid-tight container, it is possible to preserve the implant's or abutment's properties, and in particular the at least essentially monomolecular phosphate layer on the surface of the ceramic body.

In a preferred embodiment, at least part of the remaining volume of the container is filled with water and/or an inert gas. Suitable inert gases are, for instance, noble gases—preferably Ar, Ne and/or Kr—$N_2$, $O_2$ and/or $N_2O$. It has been found that by storing the dental implant or abutment of the present invention in water and/or an inert gas, it is possible to conserve the hydrophilicity of its surface. The water may be pure water or may contain one or more additives, such as $Na^+$, $K^+$, $Mg^{2+}$, $Sr^{2+}$, $Cl^-$, $PO_4^{3-}$, $HPO_4^{2-}$, and/or $H_2PO_4^-$, for instance.

Preferably, at least part of the remaining volume of the container is filled with an aqueous phosphate solution, preferably with an aqueous phosphate buffer solution. Said aqueous phosphate solution contains phosphates, typically in a concentration of 1 mM to 3 M, preferably of 20 mM to 1 M, and more preferably of 50 mM to 0.5 M, and usually has a pH of 4 to 10, preferably 5 to 9, more preferably 6 to 8. This is particularly advantageous for the at least essentially monomolecular phosphate layer on the implant's or abutment's surface.

In a further aspect, the present invention also relates to a method for the preparation of the above described dental implant or abutment. According to this method, the ceramic body of the dental implant or abutment is treated with an aqueous phosphate buffer solution and subsequently rinsed with water or an aqueous, phosphate-free solution. It is understood that prior to the rinsing with the above mentioned rinsing fluids, an optional pre-rinsing using e.g. an alcohol can be performed.

The aqueous phosphate buffer solution used for the treatment contains phosphates, typically in a concentration of 10 mM to 3 M, preferably 20 mM to 1 M, more preferably 50 mM to 1 M, and usually has a pH of 4 to 10, preferably 5 to 9, more preferably 6 to 8.

The phosphates contained in the aqueous phosphate buffer solution are selected from the group consisting of ortho-phosphate, poly-phosphates, cyclo-phosphates, and mixtures thereof. More preferably, the contained phosphates are selected from the group consisting of ortho-phosphate, di-phosphate, tri-phosphate, trimeta-phosphate, and mixtures thereof. Most preferably, the buffer solution contains ortho-phosphate.

It has been found that the rinsing time does not significantly influence the thickness of the phosphate layer obtained, as long as a certain minimal rinsing time is observed. Typically, the surface is rinsed for about 5 s to 10 min.

By performing these steps, an at least essentially monomolecular phosphate layer with a thickness of less than 1.0 nm on the ceramic surface of the body is obtained. At the same time, the surface morphology of the ceramic body is essentially preserved.

In a preferred embodiment, the dental implant or abutment further subjected to a thermal or hydrothermal treatment prior to or after the rinsing with pure water. This improves the stability of the phosphate layer on the ceramic body. Simultaneously, the dental implant or abutment is sterilised by the thermal treatment, which is particularly advantageous in view of the intended use for placement into a patient's bone.

In a preferred embodiment, the surface of the ceramic body is roughened and/or rendered hydrophilic prior to the treatment with the aqueous phosphate buffer solution. Therefore, the phosphate coating is applied to a roughened and/or hydrophilic ceramic surface.

A roughened surface may be obtained by the methods generally known in the art, such as abrasive blasting or chemical etching, for instance.

A hydrophilic surface may be obtained by the methods generally known in the art, such as chemical etching, UV irradiation or laser treatment, for instance.

It is particularly preferred that the ceramic surface is both roughened and hydrophilic. Such a surface may be obtained, for instance, by sand-blasting and subsequent acid etching, as described in EP 1 450 722. The disclosure of EP 1 450 722 regarding the preparation of a roughened and hydrophilic surface is herewith incorporated by reference. As will be shown in the examples below, a particularly long-lasting hydrophilicity can be achieved by the phosphate layer of the present invention if the body has previously been subjected to a roughening treatment, such as the one mentioned above.

Preferably, the implant or abutment of the present invention is subsequently placed in a gas- and liquid-tight container. This protects the implant or abutment during transport and storage.

The present invention is further characterized by way of the following examples:

EXAMPLE 1

Preparation of a Thick Phosphate Coating (State of the Art)

Preparation of Samples

Smooth $ZrO_2$ discs (Tosoh from Ceramtec) with a diameter of 14 mm having a polished surface were cleaned with a basic, phosphate-free cleaning agent (Deconex 15PF from Max F. Keller GmbH, Mannheim) and subjected to ultra sonication for 5 min and to oxygen plasma cleaning (using an apparatus of the type "Femto" by Diener Electronics GmbH+Co. KG, Ebhausen, Germany; 35 W, 6 sccm ("standard cubic centimeter per minute"; 1 $cm^3$ per minute at normal pressure, i.e. 1013 mbar) $O_2$ gas flow, p≈0.1 mbar, time=2.5 minutes).

The cleaned discs were immersed in 10 ml of 0.5 M Na-phosphate buffer (pH=7.2) in glass test tubes and subjected to hydrothermal treatment (121° C., 20 min) in the autoclave.

Without rinsing, the discs were dried by heating to 60° C. for 1 h.

Surface Morphology

Figure 1A:
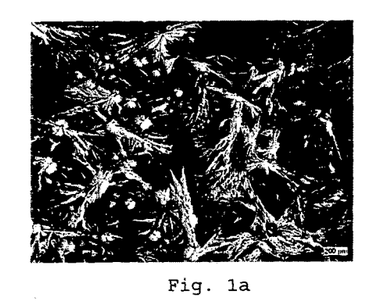
FIGS. 1a, 1b, and 1c show the surface morphology of zirconia discs with a phosphate coating of several micrometers (state of the art).
Figure 1B:
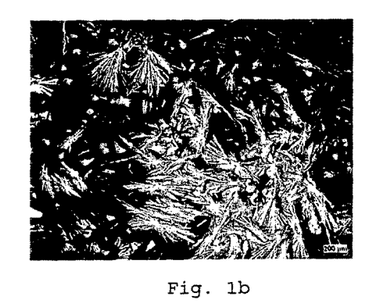
Figure 1C:
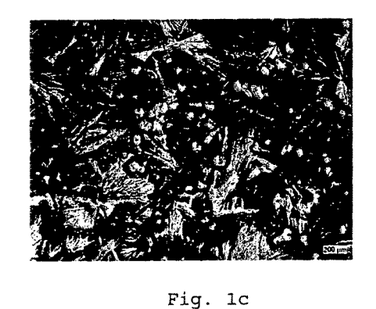

The surface morphology of the discs was investigated with an optical microscope. Images were taken with 50× magnification. FIGS. 1a, 1b, and 1c show the surface of three different discs treated in the above described way.

As can be clearly seen from these images, a relatively thick, inhomogeneous phosphate coating has formed on the ceramic surface and completely covers this surface.

Thickness of Phosphate Layer

The thickness of the phosphate coatings was determined as being in the micrometer range. Determination was performed for three samples using confocal microscopy and the following results were obtained:

Sample 1:≈4 to 5 μm
Sample 2:≈20 to 25 μm
Sample 3:≈15 μm

EXAMPLE 2

Preparation of an Essentially Monomolecular Ortho-Phosphate Layer (Rinsing by Immersion)

Preparation of Samples

Smooth $ZrO_2$ discs (Tosoh from Ceramtec) with a diameter of 14 mm having a polished surface were cleaned with a basic, phosphate-free cleaning agent (Deconex 15PF from Max F. Keller GmbH, Mannheim) and subjected to ultra sonication for 5 min and to oxygen plasma cleaning (using an apparatus of the type "Femto" by Diener Electronics GmbH+Co. KG, Ebhausen, Germany; 35 W, 6 sccm $O_2$ gas flow, p≈0.1 mbar, time=2.5 minutes).

The cleaned discs were immersed in 10 ml of 0.5 M Na-phosphate buffer (pH=7.2) in glass test tubes and subjected to hydrothermal treatment (121° C., 20 min) in the autoclave.

The treated discs were then rinsed with ultrapure water: Two glass beakers were filled with water (300 ml each) and the discs were immersed for about 5 s in each of the beakers while performing slow swirling movements.

The surface was then blown dry in a stream of Ar.

Surface Morphology

Figure 2A:
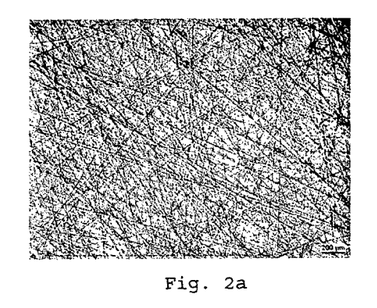
FIGS. 2a, 2b, and 2c show the surface morphology of zirconia discs with an essentially monomolecular phosphate layer according to the present invention.
Figure 2B:
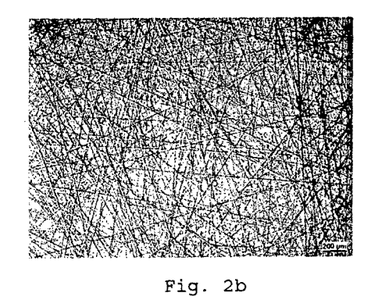
Figure 2C:
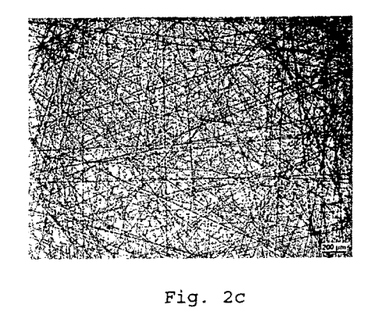

The surface morphology of the discs was investigated with an optical microscope. Images were taken with 50× magnification. FIGS. 2a, 2b, and 2c show the surface of three different discs treated in the above described way.

In these images, the phosphate layer on the ceramic surface is invisible and the morphology of the ceramic surface is essentially unchanged.

Surface Composition

The chemical composition of the surface was determined by XPS and is represented below:

| # | Zr [%] | P [%] | Y [%] | C [%] | N [%] | O [%] | Si [%] | Al [%] |
|---|---|---|---|---|---|---|---|---|
| 3 | 23.4 | 2.7 | 1.5 | 14.7 | 0.3 | 54.4 | 2.0 | 0.9 |
| 4 | 23.7 | 2.8 | 1.4 | 18.6 | 0.9 | 50.7 | 0.8 | 0.8 |

Thickness of Phosphate Layer

Based on the above atomic concentrations, the thickness of the phosphate layers was calculated based on the following assumptions:

Tetragonal structure of $ZrO_2$, (101) surface (unit cell 3.6 Å×3.6 Å×5.18 Å; 2 Zr, 4 O)

→$n_{Zr,101}$=7.58 atoms/nm$^2$; interlayer distance $d_{Zr,101}$=0.254 nm

Number of phosphate binding sites equal to number of Zr atoms on the surfaces

→$n_{P,101}$=7.58 atoms/nm$^2$ (number of binding sites equal to number of Zr atoms on the surface)

Electron mean free path: λ=3.47 nm

The thickness of the phosphate layer was then calculated using the following equation:

$$z = \lambda \cdot \cos\theta \cdot \ln\left(\frac{I_{overlayer} \cdot n_{substrate}}{I_{substrate} \cdot n_{overlayer}} + 1\right) \cdot \frac{1}{d_{Zr,101}}$$

(θ being the electron emission angle; in the present case θ=45°)

Based on the average values of the above two samples, the thickness of the phosphate layer was determined as 1.1 monolayers.

EXAMPLE 3

Preparation of an Essentially Monomolecular Ortho-Phosphate Layer (Rinsing under Running Water)

Preparation of Samples

Smooth $ZrO_2$ discs (Tosoh from Ceramtec) with a diameter of 14 mm having a polished surface were cleaned with a basic, phosphate-free cleaning agent (Deconex 15PF from Max F. Keller GmbH, Mannheim) and subjected to ultra sonication for 5 min and to oxygen plasma cleaning (using an apparatus of the type "Femto" by Diener Electronics GmbH+Co. KG, Ebhausen, Germany; 35 W, 6 sccm $O_2$ gas flow, p≈0.1 mbar, time=2.5 minutes).

The cleaned discs were immersed in 10 ml of 0.5 M Na-phosphate buffer (pH=7.2) in glass test tubes and subjected to hydrothermal treatment (121° C., 20 min) in the autoclave.

The treated discs were then rinsed under running water for about 30 s and blown dry in a stream of Ar.

Surface Composition

The chemical composition of the surface was determined by XPS and is represented below:

| # | Zr [%] | P [%] | Y [%] | C [%] | N [%] | O [%] | Si [%] | Al [%] |
|---|---|---|---|---|---|---|---|---|
| 5 | 23.8 | 2.6 | 1.4 | 19.4 | 1.2 | 49.9 | 0.7 | 1.0 |
| 6 | 22.7 | 2.1 | 1.2 | 19.4 | 0.1 | 51.4 | 2.0 | 0.7 |

Thickness of Phosphate Layer

The thickness of the phosphate layer was calculated according to the method described in example 2. Based on the average values of the above two samples, the thickness of the phosphate layer was determined as 0.9 monolayers.

EXAMPLE 4

Preparation of an Essentially Monomolecular Ortho-Phosphate Layer (Rinsing and Ultra Sonification)

Preparation of Samples

Smooth $ZrO_2$ discs (Tosoh from Ceramtec) with a diameter of 14 mm having a polished surface were cleaned with a basic, phosphate-free cleaning agent (Deconex 15PF from Max F. Keller GmbH, Mannheim) and subjected to ultra sonication for 5 min and to oxygen plasma cleaning (using an apparatus of the type "Femto" by Diener Electronics GmbH+Co. KG, Ebhausen, Germany; 35 W, 6 sccm $O_2$ gas flow, p≈0.1 mbar, time=2.5 min).

The cleaned discs were immersed in 10 ml of 0.5 M Na-phosphate buffer (pH=7.2) in glass test tubes and subjected to hydrothermal treatment (121° C., 20 min) in the autoclave.

The treated discs were then rinsed with ultrapure water: Two glass beakers were filled with water (300 ml each) and the discs were immersed for about 5 s in each of the beakers while performing slow movements. Subsequently, the discs were subjected to ultra sonification for 5 min in water at room temperature, followed by a further round of rinsing as before.

Surface Composition

The surface was then blow dried in a stream of Ar.

The chemical composition of the surface was determined by XPS and is represented below:

| # | Zr [%] | P [%] | Y [%] | C [%] | N [%] | O [%] | Si [%] | Al [%] |
|---|---|---|---|---|---|---|---|---|
| 7 | 24.6 | 2.1 | 1.6 | 18.8 | 0.4 | 50.4 | 0.9 | 1.0 |
| 8 | 25.0 | 2.2 | 1.6 | 17.0 | 0.1 | 52.6 | 0.8 | 0.7 |

Thickness of Phosphate Layer

The thickness of the phosphate layer was calculated according to the method described in example 2. Based on the average values of the above two samples, the thickness of the phosphate layer was determined as 0.80 monolayers.

EXAMPLE 5

Contact Angle Measurement of Samples Having a Thin Phosphate Layer (HF Etching of Ceramic Substrate Prior to Phosphate Coating)

$ZrO_2$ discs (MZ111 from Ceramtec) with a diameter of 15 mm were cleaned according to Examples 1 to 4. The cleaned samples were then treated as follows:

A (According to the Present Invention):
etching with HF followed by rinsing with pure water and
I) immersion in test glass in 0.5 M Na-phosphate buffer (pH=7.2)
or
II) immersion in test glass in 0.1 M Na-phosphate buffer (pH=7.2)

B (Reference):
etching with HF followed by rinsing with pure water and storage in pure water Surface Composition For XPS characterization, the samples were stored in the phosphate buffer for 2 days and then rinsed in ultrapure water followed by blow drying in a stream of Ar.

For the samples according to the present invention (two samples for each concentration), the following surface composition has been determined by XPS:

| # | Zr [%] | P [%] | Y [%] | C [%] | N [%] | O [%] | F [%] |
|---|---|---|---|---|---|---|---|
| A.I, 01 | 31.5 | 2.3 | 1.4 | 7.0 | 0.3 | 56.8 | 0.8 |
| A.I, 02 | 31.4 | 2.2 | 1.2 | 6.9 | 0.7 | 56.7 | 0.8 |
| A.II, 01 | 28.6 | 2.1 | 1.2 | 16.4 | 0.7 | 50.4 | 0.6 |
| A.II, 02 | 29.8 | 2.2 | 1.3 | 12.6 | 0.4 | 53.0 | 0.8 |

Thickness of Phosphate Layer

The thickness of the phosphate layer was calculated according to the method described in example 2. Based on the average values of the above samples, the thickness of the phosphate layer was determined as 0.7 monolayers for sample A.I and 0.7 monolayers sample A.II.

Contact Angle

The contact angle measurements were performed using a sessile drop test with ultrapure water (EasyDrop DSA20E, Krüss GmbH). The samples were analysed after different immersion times of 1 day and 22 days in phosphate buffer. The samples analysed after 1 day were afterwards stored dry and remeasured at later time points (6 d, 13 d, 21 d storage in air). The samples stored in liquid were rinsed with ultrapure water (two glass beakers filled with water, about 5 seconds rinsing in each by immersing the samples and performing slow movements) and blown dry in a stream of Ar right before analysis.

The results of the contact angle measurements are shown below. The reference samples were kept in water up to the first analysis (0 d) in order to avoid air exposure and to have the same starting point as for the samples having a phosphate layer according to the present invention.

| Sample | Storage period | Contact angle 1 | Contact angle 2 |
|---|---|---|---|
| B (ref) | 0 d | 0° | 0° |
| B (ref) | 6 d; air | 4.6° | 5.4° |
| B (ref) | 13 d; air | 17.6° | 11.6° |
| B (ref) | 21 d; air | 65° | 24.7° |
| A. II | 22 d; liquid | 0° | 0° |
| A. I | 1 d; liquid | 0° | 0° |
| A. I | 22 d; liquid | 0° | 0° |
| A. I | 6 d; air | 0° | 0° |
| A. I | 13 d; air | 0° | 2° |
| A. I | 21 d; air | 1.6° | 1.5° |

For each treatment method and time point, the contact angles of two different samples have been measured (contact angles 1 and 2, respectively).

All samples were hydrophilic right after preparation; they showed complete wetting and thus contact angles of 0°.

The contact angles of the reference samples increased with additional storage time in air.

In comparison, the samples according to the present invention, which were covered with a phosphate layer, remained super-hydrophilic with contact angles below 5°, even after a storage period of 21 d in air.

EXAMPLE 6

Preparation and Initial Surface Contact Angles of an Essentially Monomolecular Ortho-Phosphate Layer (Sand-Blasted and Acid Etched)

Preparation of Samples

Smooth $ZrO_2$ discs (Y-TZP, Yttria stabilized zirconia) with a diameter of 5 mm having a machined surface were cleaned with a basic, phosphate-free cleaning agent (Deconex 15PF from Max F. Keller GmbH, Mannheim) and subjected to ultra sonication for 5 min (no oxygen plasma cleaning).

The discs were then subjected to sand-blasting with corundum and acid treatment with HF in order to roughen the surface.

The treated discs were immersed in 20 ml of 0.1 M Na-phosphate buffer (pH=7.2; 3.37 ml 85% $H_3PO_4$, 3.4 g NaOH, pH adjustment with 1 M NaOH) in a 25 ml Schott Glass (Duranglas) and subjected to hydrothermal treatment (121° C., 20 min).

The treated discs were then rinsed under running water and blown dry in a stream of $N_2$.

Surface Composition

The chemical composition of the surface was determined by XPS and is represented below:

| # | Zr [%] | P [%] | Y [%] | C [%] | N [%] | O [%] | Na [%] | Al [%] | Mg [%] | Cl [%] | F [%] | Ca [%] |
|---|---|---|---|---|---|---|---|---|---|---|---|---|
| 9 | 26.1 | 3.8 | 0.9 | 11.3 | 0.6 | 54.6 | 0.0 | 1.9 | 0.1 | 0.0 | 0.5 | 0.2 |
| 10 | 25.0 | 3.9 | 0.9 | 11.3 | 0.5 | 55.1 | 0.6 | 1.6 | 0.0 | 0.0 | 1.1 | 0.0 |
| 11 | 26.0 | 3.6 | 0.9 | 9.5 | 1.2 | 54.8 | 0.5 | 1.7 | 0.2 | 0.0 | 0.8 | 0.8 |

Thickness of Phosphate Layer

The thickness of the phosphate layer was calculated according to the method described in example 2. Based on the average values of the above three samples, the thickness of the phosphate layer was determined as 1.3 monolayers.

Initial Surface Contact Angles

The contact angles measurements were performed with the EasyDrop DSA20E (Krüss GmbH) using a sessile drop test with ultrapure water. Three samples were measured for each surface type. The samples stored in liquid were blown dry in a stream of Ar prior to the measurement. After the measurement of the contact angle, all samples were properly rinsed under running water, blown dry with Ar and remeasured. The droplet size for the contact angle measurements was 0.1 µl for all samples. The contact angles were determined using the circle fitting procedure (fitting of a circular segment function to the contour of the droplet placed on the surface) implemented in the software.

The samples "Phosphate" were prepared as described above (present example); the samples "Comparison" were $ZrO_2$ discs from the same source, which were sandblasted and acid etched but not treated with a phosphate buffer.

The results of the contact angle (CA) measurements are compiled in the following table. The left part of the table presents the results of the contact angle measurements after blowing dry those samples stored in liquid. The right part of the table presents the results after rinsing all the samples with water and blowing dry with Ar.

| | Sample 1 CA [°] | Sample 2 CA [°] | Sample 3 CA [°] | Sample 1 CA [°] | Sample 2 CA [°] | Sample 3 CA [°] |
|---|---|---|---|---|---|---|
| Phosphate | 0 | 0 | 0 | 0 | 0 | 0 |
| Comparison | 53.5 | 66.7 | 8.7 | 20.3 | 30.0 | 7.6 |

EXAMPLE 7

Preparation and Surface Contact Angles of an Essentially Monomolecular Ortho-Phosphate Layer (Sand-Blasted and Acid Etched)

Preparation of Samples

Smooth $ZrO_2$ discs (Y-TZP, yttria stabilized zirconia) with a diameter of 5 mm having a machined surface were cleaned with a basic, phosphate-free cleaning agent (Deconex 15PF from Max F. Keller GmbH, Mannheim) and subjected to ultra sonication for 5 min (no oxygen plasma cleaning).

The discs were then subjected to sand-blasting with corundum and acid treatment with HF in order to roughen the surface.

The cleaned discs were immersed in 20 ml of 0.1 M Na-phosphate buffer (pH=7.2; 3.37 ml 85% $H_3PO_4$, 3.4 g NaOH, pH adjustment with 1 M NaOH) in a 25 ml Schott Glass (Duranglas) and subjected to hydrothermal treatment (121° C., 20 min).

Surface Contact Angles

The contact angles measurements were performed with the EasyDrop DSA20E (Krüss GmbH) using a sessile drop test with ultrapure water. Two samples were measured for each surface type. The samples stored in liquid were blown dry in a stream of Ar prior to the measurement. After the measurement of the contact angle, all samples were properly rinsed under running water, blown dry with Ar and remeasured. The droplet size for the contact angle measurements was 0.1 µl for all samples. The contact angles were determined using the circle fitting procedure (fitting of a circular segment function to the contour of the droplet placed on the surface) implemented in the software.

The samples "Phosphate" were prepared as described above (present example); the samples "Comparison" were $ZrO_2$ discs from the same source, which were sandblasted and acid etched but not treated with a phosphate buffer.

The results of the initial contact angle (CA) measurements are compiled in the first table below. The left part of the first table presents the results of the contact angle measurements after blowing dry those samples stored in liquid. The right part of the table presents the results after rinsing all the samples with water and blowing dry with Ar.

| | Sample 1 CA [°] | Sample 2 CA [°] | Sample 1 CA [°] | Sample 2 CA [°] |
|---|---|---|---|---|
| Phosphate | 0 | 0 | 0 | 0 |
| Comparison | 45.2 | 50.2 | 32.2 | 12.2 |

The contact angles of the same samples were measured once again after storing the rinsed and blown dry samples in air for 19 days. The results of the contact angle measurements after 19 days of air storage are shown in the second table below:

| | Sample 1 CA [°] | Sample 2 CA [°] |
|---|---|---|
| Phosphate | 31.4 | 18.9 |
| Comparison | 99 | 103.7 |

As can be seen from the above results, the surface of the zirconium oxide discs covered with an essentially monomolecular phosphate layer is not only significantly more hydrophilic in the initial stage, but this hydrophilicity is somewhat conserved even during prolonged storage in air. The zirconium oxide discs without phosphate coating turn completely hydrophobic within these 19 days.

Figures

The invention claimed is:

1. A dental implant or abutment comprising a ceramic body comprising zirconia as the main component, the ceramic body having a surface, wherein:
   at least a first surface area of the ceramic body is covered with a phosphate layer having a thickness in a range of from 0.7 to 1.3 phosphate molecules,
   the phosphate layer contains phosphates selected from the group consisting of ortho-phosphate, polyphosphates, cyclo-phosphates, and mixtures thereof, and
   the phosphate layer does not change a surface morphology of the ceramic body.

2. The dental implant or abutment according to claim 1, wherein the ceramic body is covered with a monomolecular phosphate layer.

3. The dental implant or abutment according to claim 1, wherein the phosphate layer has a thickness of about 0.5 nm.

4. The dental implant or abutment according to claim 1, wherein the phosphates in the phosphate layer are selected from the group consisting of ortho-phosphate, di-phosphate, tri-phosphate, trimeta-phosphate, and mixtures thereof.

5. The dental implant according to claim 1, wherein the dental implant comprises a bone contact surface area and optionally also a soft tissue contact surface area, and wherein at least the bone contact surface area is covered with the phosphate layer.

6. The dental implant according to claim 5, wherein the soft tissue contact surface area is also covered with the phosphate layer.

7. The dental implant according to claim 1, wherein the dental implant comprises an anchoring part for anchoring the dental implant in a jaw bone and a mounting part for attaching a suprastructure, and at least the anchoring part is covered with the phosphate layer.

8. The dental implant or abutment according to claim 1, wherein an entirety of the surface of the ceramic body is covered with the phosphate layer.

9. The dental implant or abutment according to claim 1, wherein the ceramic body is made of stabilized zirconia.

10. The dental implant or abutment according to claim 9, wherein the ceramic body is made of yttria-stabilized zirconia, ceria-stabilized zirconia, magnesium oxide stabilized zirconia, or alumina-stabilized zirconia.

11. The dental implant or abutment according to claim 1, wherein the dental implant or abutment is stored in water optionally containing one or more additives.

12. The dental implant or abutment according to claim 11, wherein the dental implant or abutment is stored in an aqueous phosphate solution.

13. The dental implant or abutment according to claim 12, wherein the aqueous phosphate solution is an aqueous phosphate buffer solution.

14. The dental implant or abutment according to claim 1, wherein the phosphate layer does not change a topography of the surface of the ceramic body.

15. The dental implant or abutment according to claim 1, wherein the phosphates occupy at least 10% of adsorption sites on the surface of the ceramic body.

16. A kit comprising a gas- and liquid-tight container and the dental implant or abutment of claim 1, wherein the dental implant or abutment is stored in the container.

17. The kit according to claim 16, wherein at least part of the remaining volume of the container is filled with an aqueous phosphate buffer solution and/or an inert gas.

18. A method for preparing the dental implant or abutment according to claim 1, comprising:
   treating the ceramic body of the dental implant or abutment with an aqueous phosphate buffer solution, and
   subsequently rinsing the ceramic body with water or an aqueous, phosphate-free solution.

19. The method according to claim 18, further comprising subjecting the dental implant or abutment to a thermal or hydrothermal treatment prior to or after the rinsing.

20. The method according to claim 18, further comprising roughening and/or rendering hydrophilic the surface of the ceramic body prior to the treatment with the aqueous phosphate buffer solution.

* * * * *